United States Patent
Akiba

(10) Patent No.: US 9,251,718 B2
(45) Date of Patent: Feb. 2, 2016

(54) TRAINING APPARATUS

(75) Inventor: Takeshi Akiba, Kanagawa (JP)

(73) Assignee: SYSTEM INSTRUMENTS CO., LTD., Tokyo (JP)

( * ) Notice: Subject to any disclaimer, the term of this patent is extended or adjusted under 35 U.S.C. 154(b) by 198 days.

(21) Appl. No.: 14/126,974

(22) PCT Filed: Apr. 11, 2012

(86) PCT No.: PCT/JP2012/059903
§ 371 (c)(1),
(2), (4) Date: Dec. 17, 2013

(87) PCT Pub. No.: WO2013/153635
PCT Pub. Date: Oct. 17, 2013

(65) Prior Publication Data
US 2014/0113261 A1 Apr. 24, 2014

(51) Int. Cl.
*A63B 71/00* (2006.01)
*G09B 19/00* (2006.01)
(Continued)

(52) U.S. Cl.
CPC ............ *G09B 19/00* (2013.01); *A63B 23/0405* (2013.01); *A63B 24/0003* (2013.01); *A63B 24/0087* (2013.01); *A63B 21/062* (2013.01); *A63B 2024/0012* (2013.01); *A63B 2024/0068* (2013.01); *A63B 2024/0093* (2013.01);
(Continued)

(58) Field of Classification Search
CPC .............. A63B 24/00; A63B 2024/012; A63B 2024/0068; A63B 2024/0093; A63B 2220/13; A63B 2220/17; A63B 2220/30; A63B 2220/40; A63B 2220/803; A63B 2220/805; A63B 2220/836; A63B 21/062; A63B 24/0003; A63B 24/0087
See application file for complete search history.

(56) References Cited

U.S. PATENT DOCUMENTS 5,715,160 A 2/1998 Plotke
6,656,091 B1 12/2003 Abelbeck et al.
(Continued)

FOREIGN PATENT DOCUMENTS

JP A-2000-325497 11/2000
JP A-2001-276275 10/2001
(Continued)

OTHER PUBLICATIONS

International Search Report issued in International Patent Application No. PCT/JP2012/059903 mailed Jun. 5, 2012.
(Continued)

*Primary Examiner* — Glenn Richman
(74) *Attorney, Agent, or Firm* — Oliff PLC

(57) ABSTRACT

The training apparatus includes a training machine, a detection means, and an arithmetic means. The training machine has a displacement unit displaced according to a training action and a load generation unit that imparts a load to a trainee. The detection means detects displacement of the displacement unit. The arithmetic means acquires at least one characteristic value possessed by a waveform corresponding to one unit of a training action which waveform is included in the displacement detected in the detection unit on a time axis, for each waveform, and to evaluate the acquired characteristic values for at least one of variation, transition tendency, and deviation from a predetermined value. The arithmetic means executes, based on the evaluation, at least one of control of the load generation unit, calculation of a load value set in the load generation unit, and notification of a result of the evaluation.

8 Claims, 8 Drawing Sheets

(51) Int. Cl.
*A63B 23/04* (2006.01)
*A63B 24/00* (2006.01)
*A63B 21/062* (2006.01)
*G06F 19/00* (2011.01)

(52) U.S. Cl.
CPC ......... *A63B 2220/13* (2013.01); *A63B 2220/17* (2013.01); *A63B 2220/30* (2013.01); *A63B 2220/40* (2013.01); *A63B 2220/803* (2013.01); *A63B 2220/805* (2013.01); *A63B 2220/836* (2013.01); *G06F 19/3481* (2013.01)

(56) References Cited

U.S. PATENT DOCUMENTS

| | | |
|---|---|---|
| 2006/0264299 A1 | 11/2006 | Farinelli et al. |
| 2007/0224582 A1 | 9/2007 | Hayashino et al. |
| 2011/0034300 A1* | 2/2011 | Hall .................. A63B 5/11 482/1 |
| 2011/0077127 A1 | 3/2011 | Ishii et al. |
| 2011/0077128 A1 | 3/2011 | Hamada et al. |
| 2015/0165272 A1* | 6/2015 | Bird .................. A63B 21/0058 482/5 |
| 2015/0258384 A1* | 9/2015 | Suzuki .............. A63B 24/0087 482/5 |

FOREIGN PATENT DOCUMENTS

| | | |
|---|---|---|
| JP | A-2005-328926 | 12/2005 |
| JP | A-2007-236557 | 9/2007 |
| JP | A-2009-45236 | 3/2009 |
| JP | A-2009-254788 | 11/2009 |
| JP | A-2011-67319 | 4/2011 |
| JP | A-2011-143266 | 7/2011 |

OTHER PUBLICATIONS

Mar. 11, 2015 Office Action issued in Chinese Patent Application No. 201280039562.6.

Mar. 31, 2015 Office Action issued in Japanese Patent Application No. 2014-509969.

International Preliminary Report on Patentability issued in International Application No. PCT/JP2012/059903 mailed on Oct. 16, 2014.

Oct. 16, 2015 Extended European Search Report issued in European Application No. 12874256.6.

* cited by examiner

Fig. 4
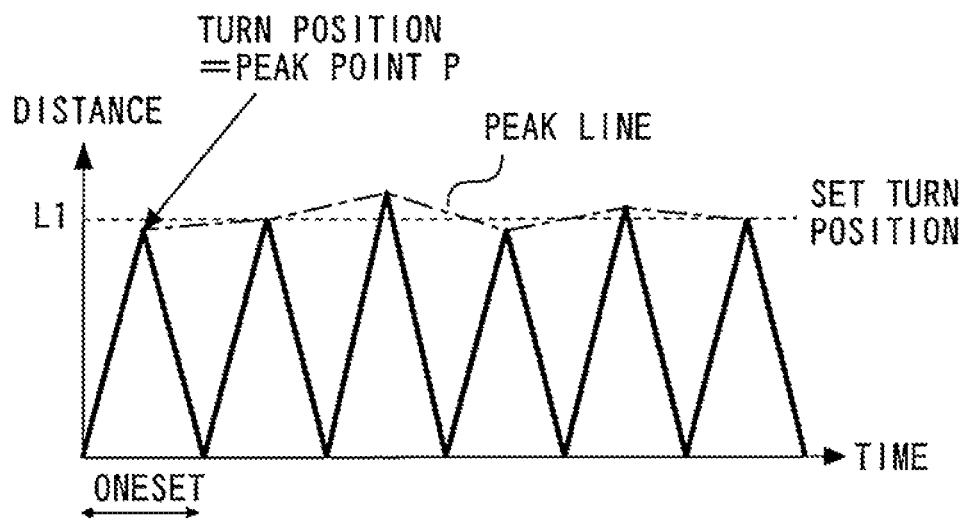
Fig..5
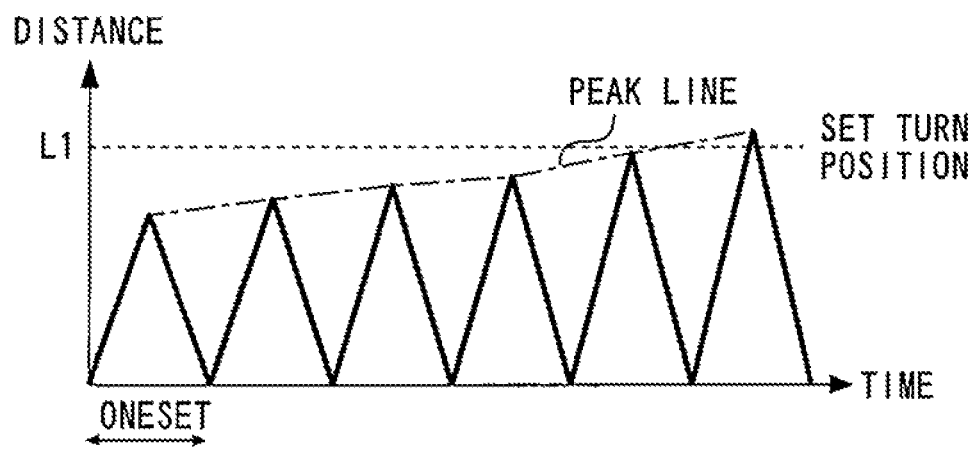

TRAINING APPARATUS

TECHNICAL FIELD

The present invention relates to a training apparatus.

BACKGROUND ART

There has conventionally been known an apparatus having a function to evaluate exercise of a trainee so as to assist a training which is performed for accomplishment of a specific purpose such as enhancing physical abilities as disclosed in Japanese Patent Laid-Open No. 2011-143266. More specifically, the gazette discloses a somatic sense exercise integrated evaluation training system, which is an apparatus having a function to evaluate particularly a motion sense among physical abilities.

CITATION LIST

Patent Literature

Patent Literature 1: Japanese Patent Laid-Open No. 2011-143266
Patent Literature 2: Japanese Patent Laid-Open No. 2005-326926
Patent Literature 3: Japanese Patent Laid-Open No. 2009-45236
Patent Literature 4: Japanese Patent Laid-Open No. 2011-67319

SUMMARY OF INVENTION

Technical Problem

When training is performed, various training apparatuses (training machines) are often used depending on purposes. The term "training" described hereinafter includes various kinds of training such as rehabilitation for elderly people or for convalescent care. There are a wide variety of situations where training is conducted. To accomplish various objects, training is conducted in various scenes including muscle training for healthy people and athletes, a preventive care for elderly people, or a convalescent rehabilitation.

In order to perform effective muscle training, it is necessary to encourage a trainee to continuously conduct a planned exercise while adding an appropriate load to the trainee in a training apparatus. This is because if the load is too heavy, an appropriate training action cannot be performed, whereas if the load is too light, a desired training effect cannot be acquired. From such a viewpoint, particularly on sites for rehabilitation and the like, a trainer or the like visually observes exercise of a trainee (a rehabilitation target person) while implementing communication with the trainee so as to adjust the weight of the load in consideration of comprehensive conditions including facial expression of the trainee. However, under such actual circumstances, a burden of the trainer or the like is increased, and the accuracy of observation and determination of adequate load adjustment cannot be improved above a certain level even with exercise observation and implementation of communication as long as they depend on ability of individuals such as trainers.

The present invention has been made to solve the above-stated problem, and an object of the present invention is to provide a training apparatus having a function to evaluate a degree of properness of a load.

Solution to Problem

A training apparatus according to the present invention, includes: a training machine, detection means, and arithmetic means. The training machine has a displacement unit displaced according to a training action and a load generation unit that imparts a load to a trainee during the training action. The detection means detects displacement of the displacement unit. The arithmetic means acquire at least one characteristic value possessed by a waveform corresponding to one unit of a training action which waveform is included in the displacement detected in the detection unit on a time axis, for each of a plurality of waveforms, to evaluate the acquired characteristic values for at least one of variation, transition tendency, and deviation from a predetermined value. The arithmetic means executes, based on the evaluation, at least one of control of the load generation unit, calculation of a load value set in the load generation unit, and notification of a result of the evaluation.

In one preferred aspect according to the present invention, the arithmetic means includes peak point specification means and calculation means. The peak point specification means specifies, as the characteristic value for each of the plurality of waveforms, a peak point that is a point where a displacement coordinate component reaches a maximum value. The calculation means controls the load generation unit or to calculate the load value which is to be set in the load generation unit based on at least one of a magnitude of variation of the specified peak points found in displacement coordinates, increase/decrease tendency of the specified peak points, and a difference of the specified peak points from a predetermined displacement.

In other preferred aspect according to the present invention, the training apparatus includes unit waveform evaluation means. The unit waveform evaluation means calculates, based on a shape of one waveform corresponding to one unit of a training action included in the displacement detected in the detection unit, the control of the load generation unit by the arithmetic means, or the load value which has been calculated by the arithmetic means and which is to be set in the load generation unit. The arithmetic means includes means configured to combine a content of the control or a content of the load value by the unit waveform evaluation means with a content of the control or a content of the load value by the arithmetic means so as to control the load generation unit or to calculate the load value which is set in the load generation unit.

In further other preferred aspect according to the present invention, the unit waveform evaluation means includes symmetry determination means and pattern determination means. The symmetry determination means determines whether or not symmetry of the one waveform is lower than a predetermined degree. The pattern determination means determines, if a waveform low in symmetry is calculated in the determination means, whether or not the waveform low in symmetry matches a predetermined pattern or approximates to the predetermined pattern at or above a predetermined level. The training apparatus further includes output means configured to output a predetermined signal if the waveform low in symmetry matches or approximates to the predetermined pattern at or above the predetermined level.

Advantageous Effects of Invention

According to the present invention, a degree of properness of a load can be evaluated based on relationship between each wave corresponding to one unit of a training action.

BRIEF DESCRIPTION DRAWINGS

FIG. 4 is a view for explaining a load control technology based on exercise states according to the embodiment of the present invention.

FIG. 5 is a view for explaining a load control technology based on exercise states according to the embodiment of the present invention.

DESCRIPTION OF EMBODIMENT

Configuration of Apparatus According to Embodiment

Figure 1:
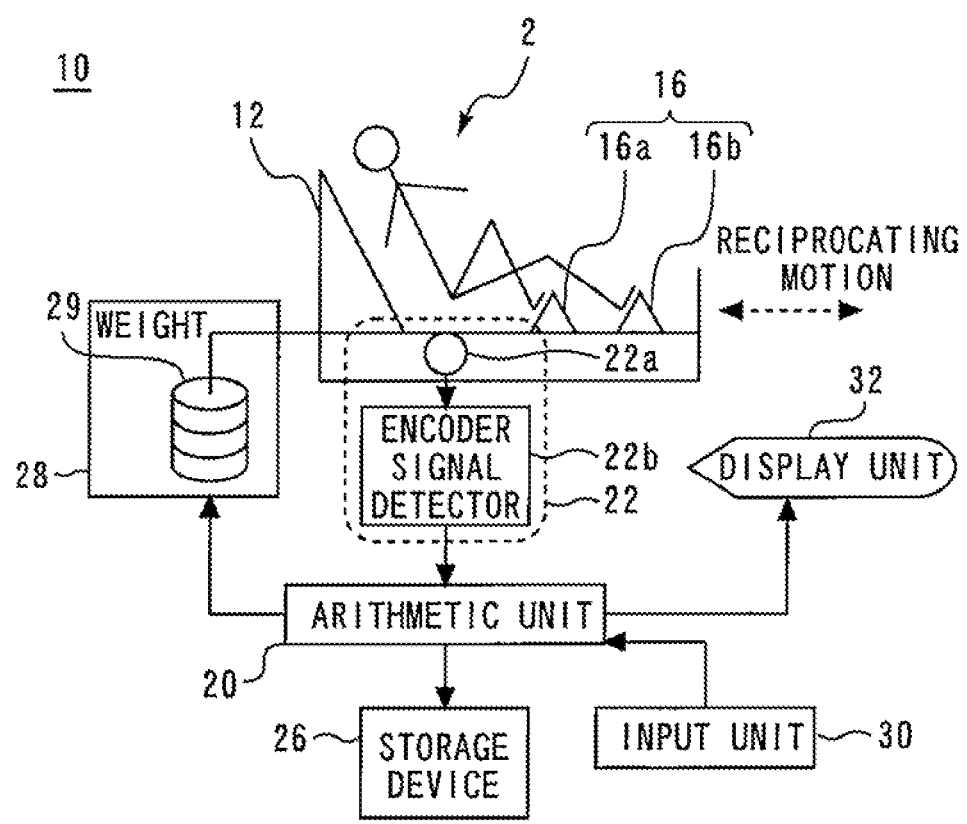
FIG. 1 is a view showing a system configuration of a training apparatus according to an embodiment 1 of the present invention.

FIG. 1 is a view showing a system configuration of a training apparatus according to an embodiment 1 of the present invention. FIG. 1 also shows a user 2 who is conducting training. The training apparatus 10 according to the present embodiment includes a muscle training machine 12. The muscle training machine 12, which allows the user to conduct so-called leg press, includes a movable unit 16 that fixes the legs of the user 2 at the time of doing the leg press. The leg press is an exercise to extend one's knee, which can strengthen muscle force of the entire lower leg and enhance the muscle force required for fundamental motions such as standing up, walking, and sitting down.

The training apparatus 10 includes an arithmetic unit 20. The arithmetic unit 20 incorporates a CPU (central processing unit), memory devices such as ROMs and RAMs, and an input/output interface that performs signal input/output to/from each device. The arithmetic unit 20 is connected to an exercise state detector 22 and an exercise load changing device 28 as well as to a storage device 26. The arithmetic unit 20 can execute an exercise state analysis calculation program preinstalled in the storage device 26. Upon reception of a signal from the exercise state detector 22, the arithmetic unit 20 can execute the exercise state analysis calculation program in cooperation with the storage device 26, and store a result of the exercise state analysis at a specified address in the storage device 26 in the form of a database. The storage device 26 may include a mass storage device such as HDDs.

The exercise state detector 22 detects the state of a training action of the user 2 while the user 2 is training with the muscle training machine 12. More specifically, an encoder 22a that detects a position of the movable unit 16 is mounted on the muscle training machine 12. The encoder 22a emits an output signal that indicates a value which increases in proportion to the position of the movable unit 16. The output signal of the encoder 22a is fed to an encoder signal detector 22b.

The encoder signal detector 22b includes a sampling circuit that samples the output signal of the encoder 22a. In this embodiment, the output signal is captured in a cycle of 50 milliseconds. The encoder signal detector 22b stores a function that associates the output signal with a distance, so that a distance L can be calculated based on the function. Thus, in response to an electrical signal from the encoder 22a, the exercise state detector 22 can detect information relating to movement of the movable unit 16 (such as a position, displacement, and a displacement velocity on a basis of a horizontal direction of the page of FIG. 1). It is to be noted that the configuration relating to an exercise state detecting device of a muscle training machine disclosed in Japanese Patent Laid-Open No. 2011-67319 may be used for the exercise state detector 22.

The exercise load changing device 28 functions as a load generation unit for adjusting a load for a leg press action in the muscle training machine 12 (more specifically, a load that prevents displacement of the movable unit 16 during implementation of training). The exercise load changing device 28 is equipped with a plurality of weights 29 as a load weight (a large number of the same load weights may be provided or a specified number of load weights different in weight may be provided). The weight 29 is linked to the movable unit 16. With this link, the load corresponding to a weight of the currently set weight 29 is imparted to the movable unit 16 and is used as the load of the leg press action. In order to implement the load which is specified with a control signal from the arithmetic unit 20, the exercise load changing device 28 combines a plurality of load weights according to a selection pattern of the load weights which is predetermined depending on an instructed magnitude of the load.

With this configuration, it becomes possible to automatically adjust the load under control of the arithmetic unit 20, without the need of requesting load adjusting operation by the user 2 or other assistants. It is to be noted that the exercise load changing device 28 may preferably be equipped with the configuration according to a load imparting apparatus for muscle training disclosed in Japanese Patent Laid-Open No. 2009-4236. It is to be noted that a device for load generation is not necessarily limited to a mechanical structure like a weight adjustment structure. A load may be imparted to the movable unit 16 by using hydraulic devices, solenoid-operated devices, and other various devices that generate resistance force based on physical principles.

The training apparatus 10 includes an input unit 30 and a display unit 32. The input unit 30 is connected with the arithmetic unit 20. The display unit 32 is more precisely a display device formed from a liquid crystal panel and the like, which outputs an exercise state analysis result obtained in the arithmetic unit 20. It is to be noted that the display unit 32 and the input unit 30 may integrally be configured as a touch panel display and the like.

Determination and control operation by apparatus according to embodiment

[Basic Data for Analysis]

FIGS. 2 through 13 are views for explaining a load control technology based on exercise states according to the embodiment of the present invention. As described in the foregoing, the training apparatus 10 according to the present embodiment is a device for performing leg press.

Figure 2:
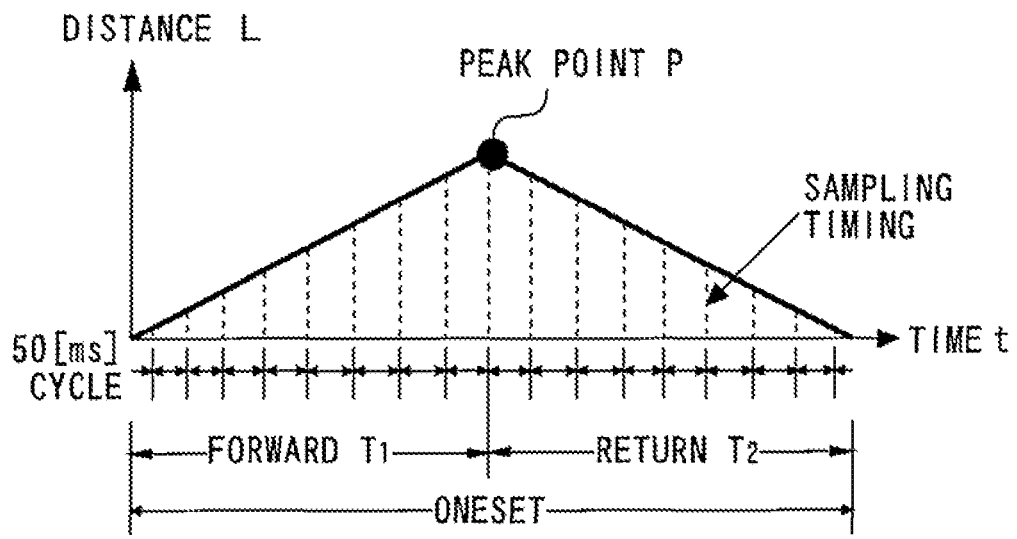
FIG. 2 is a view for explaining a load control technology based on exercise states according to the embodiment of the present invention.

The user 2 of the training apparatus 10 repeats one unit of an action made up of stretching and contracting one's legs. By this one unit of action, a value of the output signal from the encoder 22a increases for a fixed time and then starts to decrease. FIG. 2 shows this one unit of action on a two-dimensional plane made up of distance L and time t. Although a triangular waveform is illustrated as an ideal form in FIG. 2, an actual waveform is a curved waveform having some degree of a damaged symmetry since it is based on an action by the human being.

Figure 3:
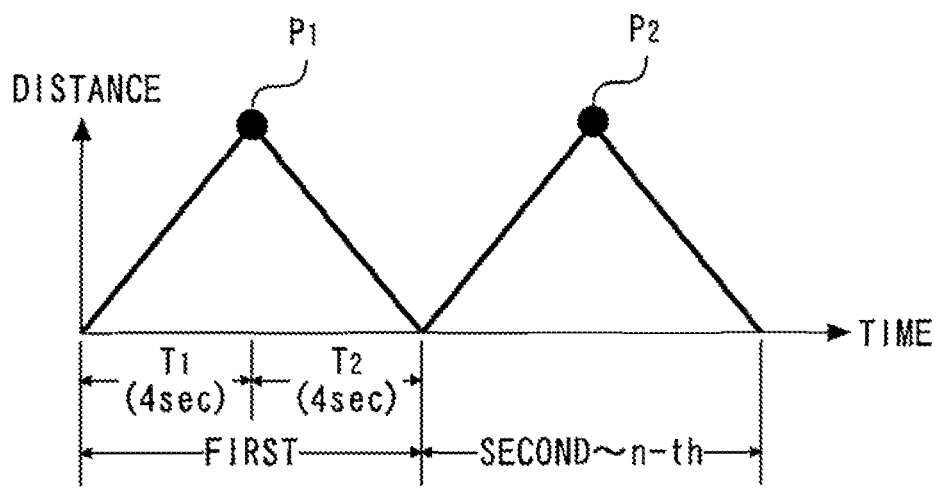
FIG. 3 is a view for explaining a load control technology based on exercise states according to the embodiment of the present invention.

As shown in FIGS. 2 and 3, the leg press action by the user 2 plots a waveform in which the distance L increases from an exercise start position (L=0) to a certain maximum value and then decreases to an original value. Hereinafter, in one unit of a reciprocating motion in the leg-press, a period when the distance L increases by leg extension is defined as time $T_1$, and a period when the distance L decreases by leg contraction is defined as time $T_2$. According to this embodiment, it is assumed that a reciprocating motion of leg press is performed by taking 4 seconds for movement in one direction (extension) and 4 seconds for return movement (contraction) in one example. A maximum value of each triangular waveform may be referred to as a peak point P, and a peak of the first reciprocating motion, the second reciprocating motion, and the n-th reciprocating motion may be referred to as P1, P2, and Pn, respectively. It is to be noted that n is a positive integer.

The training apparatus 10 can determine whether or not the load with the present weight 29 is proper by commanding the arithmetic unit 20 to execute following process (1) and process (2). The content of each process is stored in the storage device 26 as a program.

The Process (1) is a Process of Determining the Adequacy of the load based on relationship between a plurality of the peak points P.

The Process (2) is a Process of Determining the Adequacy of the load based on the symmetry in one waveform or the like.

Note that in analyzing methods and arithmetic processes (determination processes) described below, "specified values" are used for evaluation. Although different specified values are generally used for different analyzing methods and processes, the same specified value may commonly be used among a plurality of analyzing methods and processes if possible.

[Process of Determining Adequacy of Load Based on Relationship Between a Plurality of Peak Points P]

FIGS. 4 through 9 are views for explaining the content of a load adequacy determination process executed by the arithmetic unit 20 in this embodiment. In this embodiment, a prescribed number of peak points among the peak points P1, P2, . . . Pn in a plurality of the triangular waveforms are used to determine the adequacy of the load based on a positional relationship between these peaks. More specifically, in this embodiment, the positional relationship between respective peaks in six waveforms is used for the determination as shown in FIG. 4 and other drawings.

Extraction of the peak points P can be performed by monitoring the output of the encoder 22a. More specifically, as shown in FIG. 2, increase and decrease of the distance L is switched when the movement in one direction is changed to the return movement, and therefore this changing point can be extracted as a peak point P. In short, the peak point P is a turn position of the reciprocating motion on the axis of the distance L.

Although six peak points P are used for analysis in this embodiment, the number of peak points P used for analysis needs be two or more, and may be six or more.

According to this embodiment, the followings are used as the analyzing method.

(Analyzing Method 1)

Variation in a plurality of the peak points P is analyzed. In short, variation in the turn positions on the axis of the distance L is analyzed. Evaluation of the variation may be performed based on, for example, a magnitude of mean deviation. As the variation in the peak points P (variation in turn positions) is smaller, that is, as the distance axis directional component values of the peak points P are more identical, the load is considered to be more adequate. It is also possible to determine that the load is more adequate as a preset certain turn position L1 and the position of the peak point P is closer.

Figure 6:
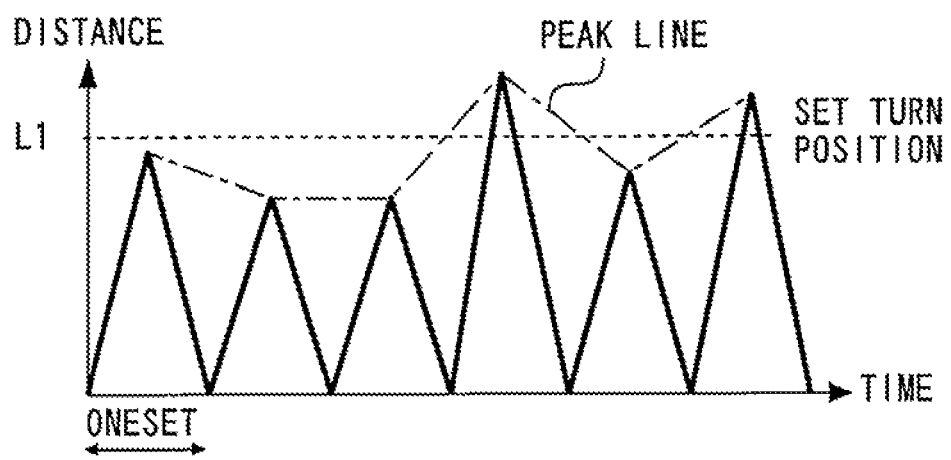
FIG. 6 is a view for explaining a load control technology based on exercise states according to the embodiment of the present invention.

In the case of the waveform shown in FIG. 4, a plurality of the turn positions (distance directional components of the peak points P) are generally in the state of being level, and each of the peak points P is close to the preset turn position (distance L1). Accordingly, in the case of FIG. 4, the load is determined to be proper and the load is not changed. Contrary to this, when the turn positions (peak points P) are irregular and uneven as shown in FIG. 6, the load is determined to be heavy, and so the load is reduced when the training is started next time or in future. More specifically, if the magnitude of a mean deviation is larger than a specified value, it is determined as shown in FIG. 6 that the load is heavy.

(Analyzing Method 2)

Here, a straight line, a polygonal line, and a curve formed to present all of a plurality of the peak points P are also referred to as "a peak line". According to this embodiment, the peak line is defined as a line formed by connecting between a plurality of the peak points P. However, the line of the present invention is not limited thereto, but a line formed by applying such a method as a least square method to a plurality of the peak points P, and a line formed by fitting a plurality of the peak points P with a straight line or a curve may also be used.

In FIG. 5, the turn positions (distance directional components of the peak points P) are gradually larger over time, and the peak line inclines upward toward the right side. Furthermore, the peak line ends up reaching the specified turn position (L1). Although it cannot be said that proper training actions are carried out with such a pattern, the load is not changed at the current moment since a factor causing this pattern is impossible to identify. Whether a training action falls within the case of FIG. 5 may be determined based on whether or not an inclination of the peak line shows increase (positive value), or whether or not the inclination is equal to or more than a specified value.

Figure 7:
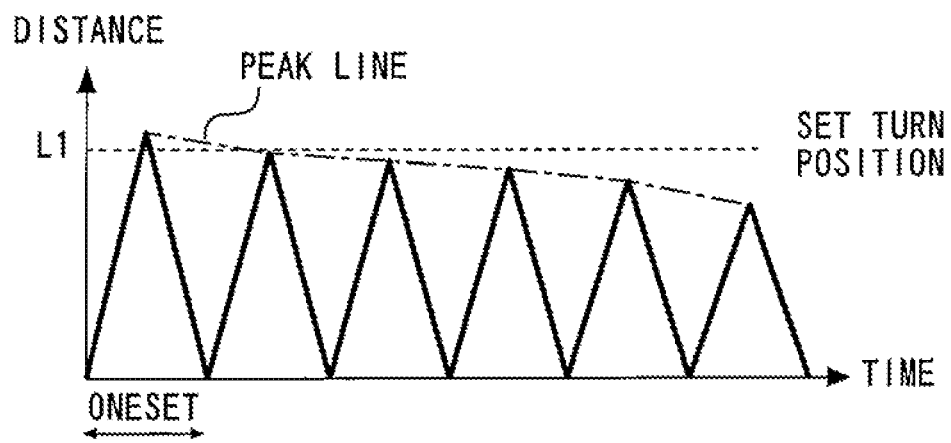
FIG. 7 is a view for explaining a load control technology based on exercise states according to the embodiment of the present invention.

In FIG. 7, the turn positions (distance directional components of the peak points P) are gradually smaller over time, and the peak line inclines downward toward the right side. In this case, it can be considered that the current load is not appropriate and is heavy for the user 2. Accordingly, the load is reduced when the training is started next time or in future. Whether a training action falls within the case of FIG. 7 may be determined based on whether or not an inclination of the peak line shows decrease (negative value), or whether or not the negative value is less than a specified value.

(Analyzing Method 3)

Figure 8:
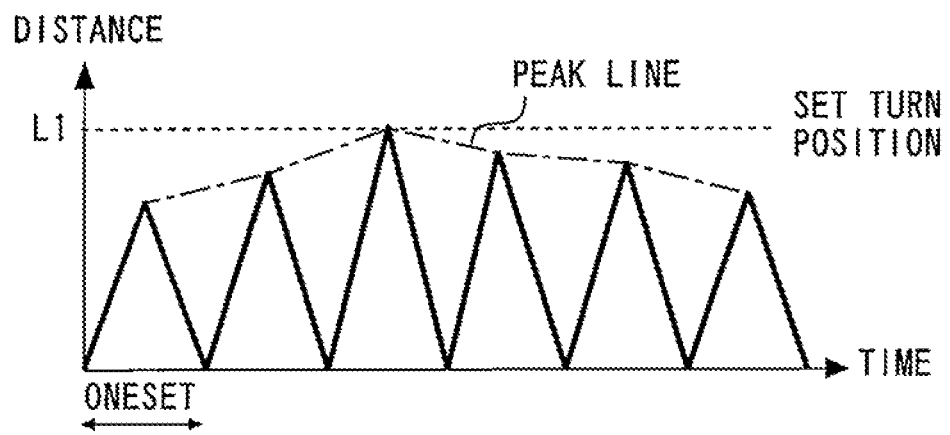
FIG. 8 is a view for explaining a load control technology based on exercise states according to the embodiment of the present invention.

In FIG. 8, the turn position distance directional components of the peak points P) have an upward trend at the beginning but start to have a downward trend in a midway, which provides a mountain-like peak line. This is considered to be caused by fatigue of the user 2 resulting from an excess of the load, and so it is determined that the load is heavy. Accordingly, the load is reduced at the time when the training is started next time or in future. Whether a training action falls within the case of FIG. 8 may be determined based on whether or not an inclination of the peak line has both the increase (positive value) and decrease (negative value), or whether or not both the positive value and the negative value are equal to or more than a specified value.

(Analyzing Method 4)

Figure 9:
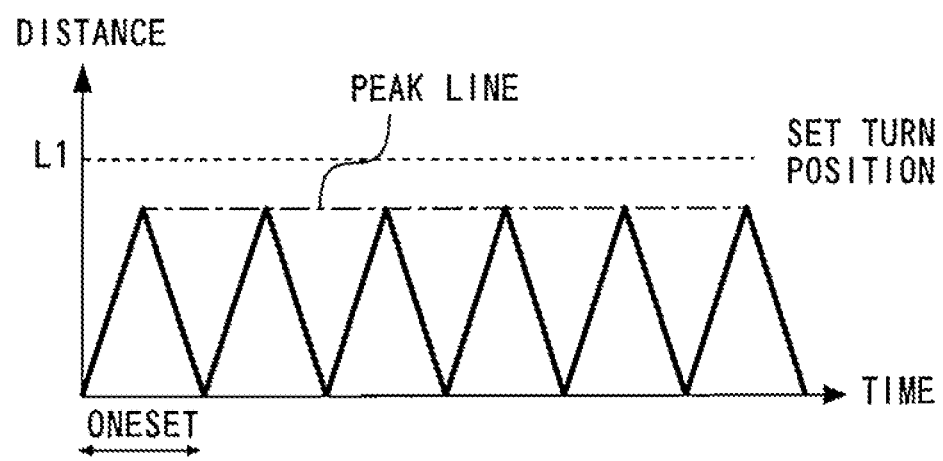
FIG. 9 is a view for explaining a load control technology based on exercise states according to the embodiment of the present invention.

FIG. 9 shows the state where all the strokes are detected as short strokes due to a setting error of the distance L1, or the like. In this case, since evaluation based on the distance L1 cannot be performed, the distance L1 is reset (reset to be a smaller value in the case of FIG. 9). Load change is not performed. Whether or not a training action falls within the case of FIG. 9 may be determined based on whether or not an average distance between the peak line and the distance L1 is larger than a specified value.

(Other Analyzing Methods)

In addition to the above described analyzing methods, another method may be used to determine the adequacy of the load, in which "an average value of strokes" is calculated and the average value is compared with a specified value. It is also possible to compare "difference between a maximum value and a minimum value of the turn position (i.e., a difference between a maximum value and a minimum value of the peak point P)" with a specified value, and to determine that the load is more adequate as the difference between the maximum value and the minimum value is smaller. It is also possible to compare "difference obtained between the peak points P of two particularly adjacent triangular waveforms", among a plurality of triangular waveforms, with a specified value, and to determine that the load is more adequate as the difference between two peak points P is smaller. It is also possible to compare "magnitude of an inclination of the peak line" with a specified inclination, and to determine that the load is more adequate as the inclination is smaller. It is also possible to compare "magnitude of a difference from a turn position to a prescribed position" with a specified value.

Analysis results obtained by the above-mentioned analyzing methods may be calculated as "adequacy parameters" that quantitatively express the adequacy of the load. For example, while the processes to compare obtained values with respective specified values have been explained in the aforementioned respective analyzing methods, it is also possible to calculate a difference from a specified value and to compute the difference and the adequacy parameters in accordance with a prescribed rule (e.g., proportionality). When a rule is so set that the load is more adequate as values of the adequacy parameters are larger, the adequacy parameters may be set to take larger values as a value of variation or the like becomes smaller.

[Process of Determining Adequacy of Load Based On Symmetry in one waveform or the like]

In this embodiment, in addition to the above-mentioned "process of determining adequacy of load based on relationship between a plurality of peak points P", the following process shall subordinately be executed as well. As a consequence, it becomes possible to reach a final conclusion or to implement more precise adequacy determination in the case where it is difficult to make determination only with the above-mentioned "process of determining adequacy of load based on relationship between a plurality of peak points P".

Figure 10:
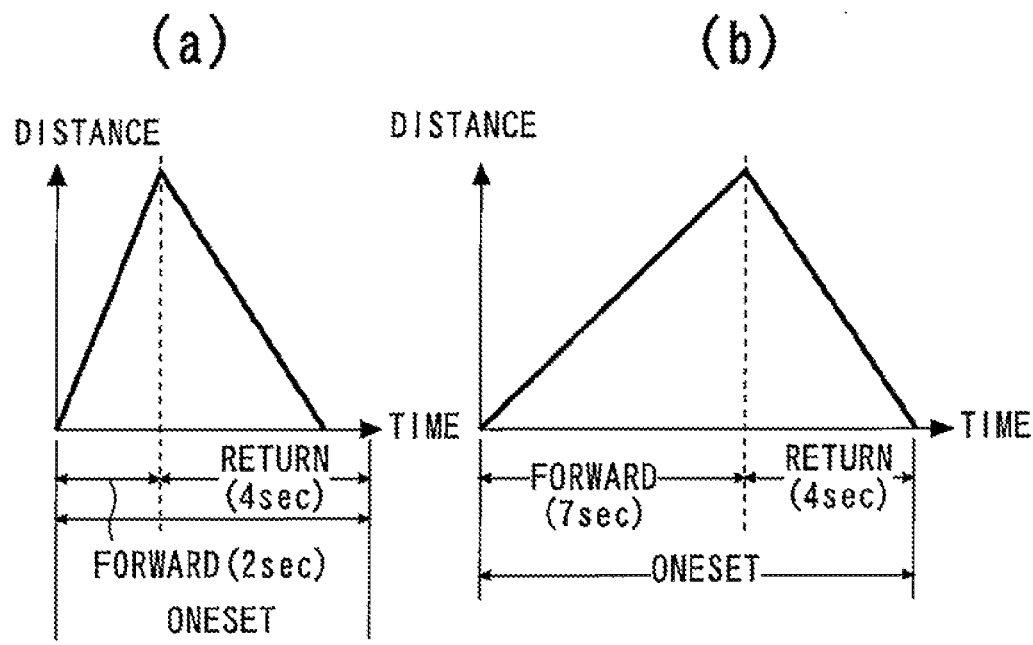
FIG. 10 is a view for explaining a load control technology based on exercise states according to the embodiment of the present invention.

FIG. 10 is a view showing one example of the load adequacy evaluation corresponding to exercise time executed by the training apparatus 10 in this embodiment. As mentioned above, it is assumed in this embodiment that leg press is a reciprocating motion made up of 4-second movement in one direction and 4-second return movement. In FIG. 10($a$), the movement in one direction takes 2 seconds, which is 2 seconds shorter than the assumed 4 seconds. On the contrary, the movement in one direction in FIG. 10($b$) takes 7 seconds, which is 3 seconds longer than the assumed 4 seconds. In this case, since deviation from a reference period of 4 seconds is larger in the result of FIG. 10($b$), it is concluded that the adequacy of the load of FIG. 10($b$) is relatively lower than that of FIG. 10($a$) and therefore the necessity for changing the load is higher. Accordingly, it is also possible to perform analysis based on such temporal relationship between the movement in one direction and the return movement.

In short, the arithmetic unit 20 may execute an exercise time determination process. The exercise time determination process is a process in which time of movement in one direction and time of return movement are compared with respective reference time and it is determined that the load is less adequate as the deviation from the reference time is larger. A computation program for the exercise time determination process is preinstalled in the storage device 26.

Figure 11:
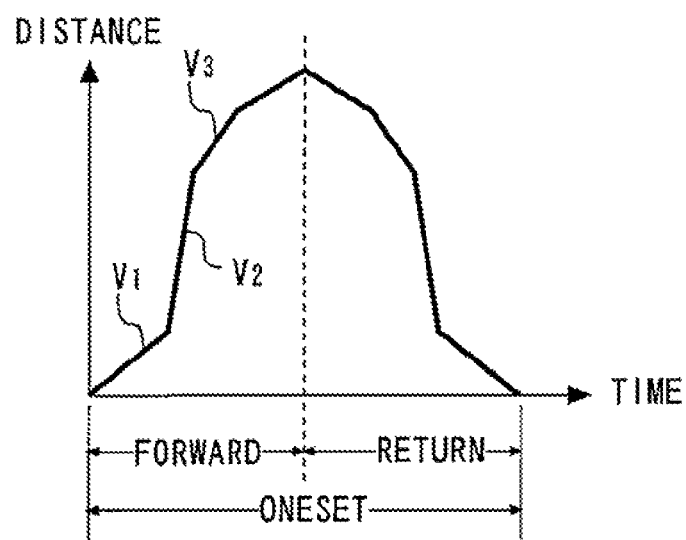
FIG. 11 is a view for explaining a load control technology based on exercise states according to the embodiment of the present invention.

FIG. 11 is a view showing one example of the load adequacy evaluation corresponding to exercise time executed by the training apparatus 10 in this embodiment. In this embodiment, a motion velocity of the training action is used as a determination element of the load adequacy evaluation. Particularly in this embodiment, it is determined that the load is more adequate as the motion velocity is changed less during the training action. A waveform shown in FIG. 11 indicates that the training action is performed at different velocities V1, V2, and V3 (i.e., distance/time). Referring to FIGS. 2 and 3, the velocity is constant, and respective inclinations in the movement in one direction and the return movement are also constant.

Accordingly, the arithmetic unit 20 may execute a velocity determination process. The velocity determination process is a process in which a velocity is calculated from relationship between the distance and the time, and if different velocities like V1, V2, and V3 are calculated and a difference in magnitude between the respective velocities is within a specified value range, then the load is determined to be adequate. A computation program for the velocity determination process is preinstalled in the storage device 26.

Figure 12:
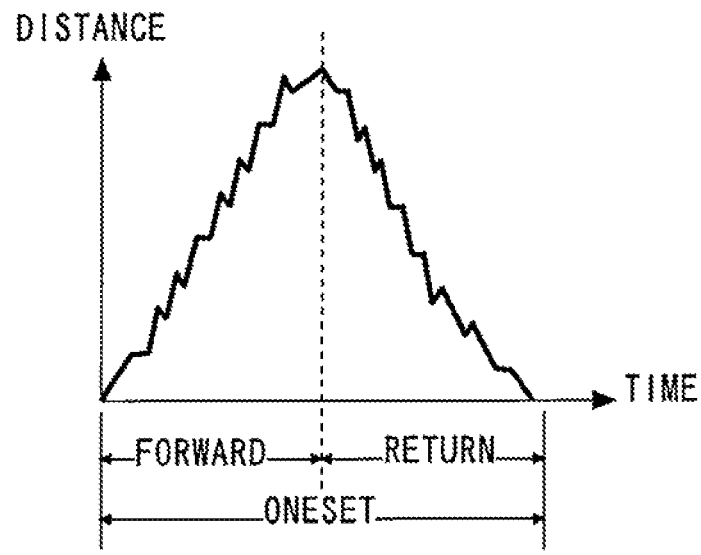
FIG. 12 is a view for explaining a load control technology based on exercise states according to the embodiment of the present invention.

FIG. 12 is a view showing one example of the load adequacy evaluation corresponding to exercise time executed by the training apparatus 10 in this embodiment. In this embodiment, smoothness (smoothness degree) of the training action is used as a determination element of the load adequacy evaluation. Particularly in this embodiment, it is determined that the load is more adequate as the smoothness during the training action is higher. In this regard, it is clear that a waveform shown in FIG. 12 is low in smoothness. The waveform is unlike the waveforms shown in FIGS. 2 and 3, where the waveforms are linear and so the smoothness is high in both the movement in one direction and the return movement.

Accordingly, the arithmetic unit 20 may execute a smoothness determination process. The smoothness determination process is a process in which publicly known various kinds of computation programs are executed to quantitatively evaluate the smoothness of a waveform, and if the calculated smoothness is within a specified value range, the load is determined to be adequate. For example, it is possible to evaluate whether or not magnitude of deviation between a smooth reference straight line and each peak in uneven portions of an actually detected line (e.g., average value) is smaller than a specified value. A computation program for the smoothness determination process is preinstalled in the storage device 26.

Figure 13:
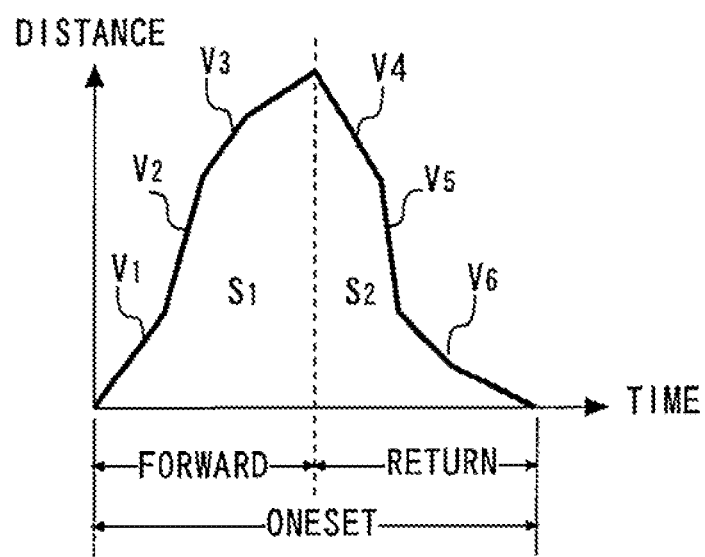
FIG. 13 is a view for explaining a load control technology based on exercise states according to the embodiment of the present invention.

FIG. 13 is a view showing one example of the load adequacy evaluation corresponding to exercise time executed by the training apparatus 10 in this embodiment. In this embodiment, the symmetry in a waveform corresponding to one unit of a training action is used as a determination element of the load adequacy evaluation. Particularly in this embodiment, it is determined that the load is more adequate as the waveform corresponding to the one unit of training action has a shape where a part corresponding to movement in one direction and a part corresponding to return movement are line-symmetric. In this regard, the waveform shown in FIG. 13 has low symmetry as compared with the waveforms shown in FIGS. 2, 3, and 11. In FIGS. 2 and 3, the waveforms are triangular waveforms having a complete line symmetry and forms isosceles triangles whose inclinations in the part corresponding to movement in one direction and the part corresponding to return movement are identical. Contrary to this, in the waveform shown in FIG. 13, the part corresponding to movement in one direction and the part corresponding to return movement are asymmetric to each other.

Accordingly, the arithmetic unit 20 may execute a symmetry determination process. The symmetry determination process is a process which includes a computing process which compares the part corresponding to movement in one direction and the part corresponding to return movement of a waveform and computes an amount of deviation thereof. In this determination process, it is determined that the symmetry is higher as the deviation amount is smaller, that is, it is determined that the load is adequate if the deviation amount is within a specified value range for example. A computation program for the symmetry determination process is preinstalled in the storage device 26.

If has been determined that the load is adequate in each of the above-mentioned exercise time determination process, the velocity determination process, the smoothness determination process, and the symmetry determination process, then the value of the load is maintained at the fixed value. In contrast, if it has been determined in some of these processes that the load is not adequate, such measures as determination by a majority or appropriate weighting may be taken so as to achieve final conclusion regarding the adequacy of the load.

If the conclusion that the load is not adequate is achieved, the arithmetic unit 20 may be made to execute a process of integrating load increase and load decrease conclusions led by the respective processes and calculating a final load adjustment amount based on, for example, determination by a majority, use of an average value, and weighting. The load adequacy parameters may also be calculated in a similar way.

[Use of Analysis Result]

(Load Control and Automatic Load Control Mode)

Once the load adequacy determination is performed by each of the above-mentioned analyzing methods, the determination result is used for actual load control by the exercise load changing device 28. With respect to the use of the result, if it has been determined that the load is adequate (proper), the training is continued with the same load, and the training may be started with the same load next time and in future. Contrary to this, if it has been determined that the load is inadequate, then the load may automatically be changed (increased or decreased based on a prescribed rule) at the time of load setting when the training is started next time and in future. The mode which automatically changes the load is referred to as "an automatic load control mode".

If it has been determined that the present load is not adequate and that the present load is heavy, then the arithmetic unit 20 calculates a load for the next time and in future so that the load is reduced. On the contrary, if it has been determined that the present load is not adequate and that the present load is light, then the arithmetic unit 20 calculates a load for the next time and in future so that the load is increased. It is to be noted that determination of a change amount of the load or a target value of the load may be implemented by setting a fixed value as one increase/decrease amount, or by calculating so as to have relationship which is proportional to the adequacy parameter values.

Note that if any disagreement or confliction is present among analysis results (adequate or not, load increase or load decrease) of a plurality of analytic algorithms, the arithmetic unit 20 may execute an adjustment process to reach a final conclusion through determination by a majority and weighting.

(Questionnaire Mode)

In the above-described explanation, the configuration of automatically adjusting the load value has been explained. However, the training apparatus 10 does not need to perform automatic adjustment of the load. In short, the configuration of using the analysis results obtained in the above-described analyzing methods may only include display of the analysis results on the display unit 32, or the analysis results may only be reflected upon the process of calculating a load set value which is a candidate value to be set as a load.

By displaying the analysis result, a determination regarding what kind of measure is taken against the analysis result, that is, a final determination regarding, for example, whether the load is maintained, increased or reduced may be made by a trainer or the user 2 him/herself. Moreover, the user 2 may arbitrarily determine whether to use the load set value calculated as a candidate. The user 2 may input from the input unit 30 whether to accept the load set value (load change) based on the determination result. This is a kind of questionnaire.

Even in such a Questionnaire mode, using a function to evaluate the degree of properness of the load makes it possible to reduce the burden of trainers and the like, and thereby makes it possible to objectively perform determination of the adequacy of load adjustment with high precision and a less burden.

It is to be noted that the analysis result may be displayed on the display unit 32 in the form of words "proper", "hard" and "easy" with use of alphabetic characters and the like. The arithmetic unit 20 executes a process of displaying on the display unit 32 the word "proper" when it has been determined that the load is adequate, the word "hard" when it has been determined that the load should be reduced, and the word "easy" when it has been determined that the load should be increased.

It is to be noted that operation modes "automatic load adjustment mode" and "questionnaire mode" at which the training apparatus 10 is operated may be switched by manual switching or by automatic switching. Even in the automatic load adjustment mode, display of the analysis result can be conducted.

Concrete Processes by Apparatus According to Embodiment

Figure 14:
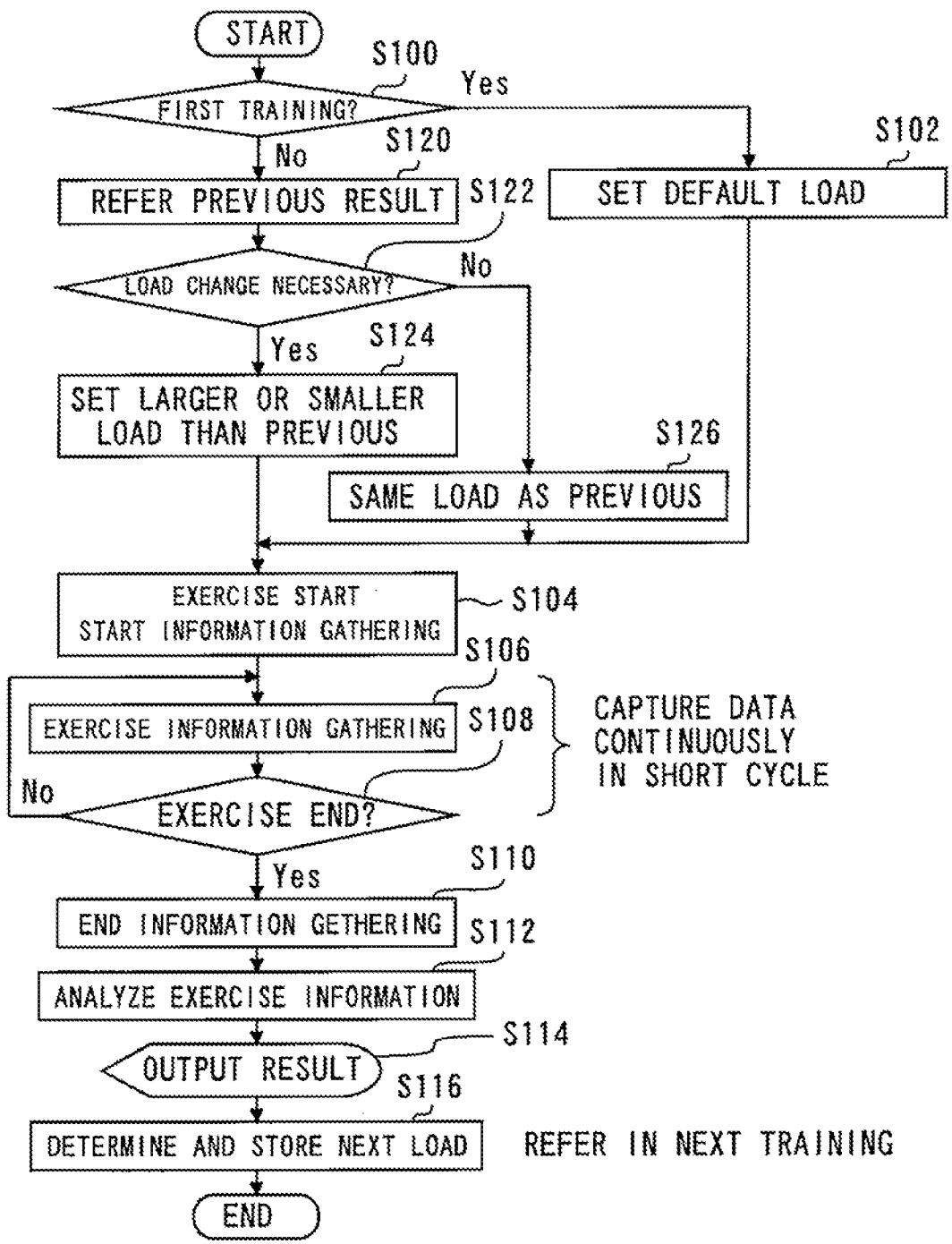
FIG. 14 is a flow chart of a routine executed by the arithmetic unit 20 of the training apparatus 10 in the embodiment of the present invention.

FIG. 14 is a flow chart of a routine executed by the arithmetic unit 20 of the training apparatus 10 in the embodiment of the present invention.

In the routine of FIG. 14, first, the arithmetic unit 20 executes a process of determining whether or not the current training is the first training (Step S100. This process may be implemented by providing a table in the storage device 26 in advance to preinstall a process of storing a training history, and executing a process of determining whether or not a previous training history is present in the table in Step S100. If the training history is not present, then it is determined that this is the first training. It is to be noted that the training history may include training date and time, ID of the user 2, and contents of the training (a load value, leg press counts, time, and other information).

If it has been determined that the training is the first training in Step S100, the arithmetic unit 20 executes a process of imparting a control signal, which is for combining weights 29, to the exercise load changing device 28 so as to assert a default load (specified value) (Step S102).

If it has been determined that the training is not the first training in Step S100, the arithmetic unit 20 executes a process of referring to the previous analysis result (Step S120). According to this embodiment, "an analysis result storage region" which stores the previous analysis result is provided in the storage device 26. The arithmetic unit 20 refers to the analysis result storage region in this step. The analysis result storage region stores the result of an exercise information analyzing process in Step S112 described later.

Next, the arithmetic unit 20 executes a process of determining whether or not load change is necessary based on the previous analysis result (Step S122). The arithmetic unit 20 refers to the analysis result storage region in this Step S122. The determination result of whether or not the load change is necessary is determined depending on the process result of the exercise information analyzing process in Step S112 described later.

If it has been determined that the load change is not necessary in Step S122, the arithmetic unit 20 executes the process of imparting a control signal to the exercise load changing device 28 so as to implement a combination of the weights 29 which provides the same load as in the previous training stored in the training history.

If it has been determined that the load change is necessary in Step S122, then the arithmetic unit 20 executes the process of imparting a control signal to the exercise load changing device 28 so as to set a load which is heavier or lighter than the load of the previous time (Step S124). The arithmetic unit 20 refers to the analysis result storage region in this step. Whether the load is set heavier or lighter than the previous time is determined depending on the process result of the exercise information analyzing process in Step S112 described later.

Next, the arithmetic unit 20 executes a process of notifying the user 2 of completion of exercise start preparation (for example, a message "ready to start exercise" is displayed on the display unit 32), and also executes a process of starting information gathering (Step S104). More specifically, the process of starting information gathering is a process in which the exercise state detector 22 starts sampling of the output signal of the encoder 22a. After Step S104, the user 2 arts exercise.

Next, the arithmetic unit 20 executes a process of gathering exercise information (Step S106). In this process, the output signal of the encoder 22a is captured in a cycle of 50 milliseconds. During this period, the user 2 performs leg press according to a predetermined training schedule.

Next, the arithmetic unit 20 executes a process of determining whether or not exercise is terminated (Step S108). In this Step, it is determined, for example, whether or not exercise termination operation is inputted from the input unit 30, and if input information regarding the current training schedule is present, it is determined whether or not the exercise count reaches the count of leg press reciprocating motions preset based on the input information. If it has been determined that the exercise is not terminated, the process loops back to Step S106, where continuous data capturing in a short period is continued.

If exercise termination has been determined in Step S108, the arithmetic unit 20 executes a process of terminating information gathering Step S110).

Next, the arithmetic unit 20 executes process of analyzing exercise information (Step S112). In this Step, the arithmetic unit 20 executes (1) process of determining adequacy of load based on relationship between a plurality of peak points P and (2) process of determining adequacy of load based on symmetry in one waveform and the like as described in "determination and control operation by apparatus according to embodiment". With these processes, the information regarding whether or not load change is necessary and the information regarding whether the load, if it is needed to be changed, should be heavier or lighter than the previous load are stored as described above in "the analysis result storage region" of the storage device 26.

Next, the arithmetic unit 20 executes a process of outputting the result (Step S114). In this step, the arithmetic unit 20 displays words "proper", "hard" and "easy" with use of alphabetic characters on the display unit 32 depending on the analysis result in Step S112.

Next, the arithmetic unit 20 executes a process of determining and storing a load for the next time (Step S116). In this step, it is determined, based on the analysis result of Step S112, whether or not the load for the next time is according to the load stored in "the analysis result storage region".

in the case of the automatic load control mode, the analysis result of Step S112 is reflected as it is. In the case of the questionnaire mode, it is possible to execute a process of encouraging information input with the input unit 30 (for example, a process of displaying a message such as "waiting for input of answers to questionnaire" on the display unit 32) in Step S114, or it is also possible to determine the final load for the next time based on input operation to the input unit 30. In other words, if the message "proper" is inputted to the input unit 30 even though the message "hard" or "easy" is displayed on the display unit 32, then the load same as the current load may be set as the load for the next time. After that, the routine is ended.

Modified Example of Apparatus According to Embodiment (Process Of Discriminating From Abnormalities Such as Nervous System Abnormality)

Although FIG. 13 shows one type of the waveform in which the load is not adequate, the waveform as shown in FIG. 13 is one of the typical waveforms obtained when the user 2 has a damaged nervous system, or the like. In the waveform shown in FIG. 13, first in the movement in one direction, the distance increases at a velocity V1, then rapidly increases at a velocity V2 (provided V1<V2), and further increases gently at a velocity V3 (provided V3<V2). Then, in the return movement, the distance decreases at a velocity V4 (provided that an absolute value of V4 is larger than an absolute value of V3), and rapidly decreases at a velocity V5 (provided that an absolute value of V5 is larger than the absolute value of V4), and then gently decrease at a velocity V6 (provided that an absolute value of V6 is smaller than the absolute value of V5). An integral value (area S1) of the waveform in the movement in one direction is larger than an integral value (area S2) of the waveform in the return movement. Compared with the waveform in the part corresponding to the movement in one direction, the waveform in the part corresponding to the return movement has a shape tapered toward the upper side of the page.

Accordingly, if a waveform low in symmetry is calculated, the arithmetic unit 20 may further determine whether or not the waveform matches (or significantly approximates to) a predetermined pattern as shown in FIG. 13. If the waveform matches (or significantly approximates to) the predetermined pattern, an analysis result indicating a possibility of abnormality in a nervous system or the like may be presented. Or alternatively, an analysis result indicating a possibility of occurrence of abnormality in training due to a factor other than the load may be presented.

A concrete determination process thereof may be implemented, for example, by the arithmetic unit 20 executing at least one of the following processes (A), (B), and (C).

The process (A) is a process of determining whether or not the waveform corresponds to the above-mentioned relationship between V1 to V6.

The process (B) is a process of determining whether or not the waveform corresponds to the relationship between areas S1 and S2.

The process (C) is a process in which the waveform is fitted to a pre-acquired waveform of a user having a nervous system abnormality and it is determined whether or not an approximation degree (matching degree) is equal to or more than a specified percentage.

In such a case, the arithmetic unit 20 may execute a process of notifying "a specific abnormality output value" which indicates that training abnormality is occurring due to a factor other than the load by displaying the value on the display unit 32 or the like, or a process of recording the value in the training history table inside the storage device 26.

It is to be noted that "the process of discriminating from abnormalities such as nervous system abnormality" may be used together with the processes (1) and (2) explained in "determination and control operation by apparatus according to embodiment" or may be used in a separate and independent manner.

In the case of using the process in the separate and independent manner, the training apparatus includes a muscle training machine 12, an exercise state detector 22, an arithmetic unit 20, and a storage device 26. If a waveform low in symmetry is calculated, the arithmetic unit 20 further executes the process of determining whether or not the symmetry comparison thereof matches (or significantly approximates to) a predetermined pattern as shown in FIG. 13. If the pattern matches (or significantly approximates to) the predetermined pattern, there is emitted an output signal representing an analysis result which indicates that there is a possibility of the nervous system abnormality or an analysis result which indicates abnormality is occurring in training due to a factor other than the load. Based on the output signal, display on the display unit 32 or notification to the outside may be performed. In that case, a process of stopping load change, which stops load change irrespective of the analysis result of the load, may be performed.

Note that in the above explanation, the discrimination process (process of discriminating from abnormalities such as nervous system abnormality) that discriminate "improper actions caused by the load" from "nervous system abnormality". Here, symptoms of the nervous system abnormality are considered to be caused by muscle defects (such as pulled muscle), bone defects (such as stress fracture), and joint defects (such as misalignment of joint surfaces). Accordingly, the aforementioned discrimination process may be offered as a determination process (process of determining abnormality such as muscle defect) which determines presence of a defect in these muscle, bone, and joint.

(Characteristic Value for Each Waveform)

In the embodiment, peak points P1, P2, . . . Pn where a displacement coordinate component becomes a maximum value are identified for each of a plurality of the waveforms obtained from an output signal of the encoder 22a. Adequacy of the load is analyzed by using the values of a plurality of the peak points P. However, the present invention is not limited to the configuration which uses the peak points P. It is also possible to acquire at least one "characteristic value" possessed by a waveform corresponding to one unit of a training action on a time axis for each of a plurality of the waveforms, and to evaluate at least one of variation, transition tendency, and deviation from a specified value with respect to a plurality of the acquired characteristic values.

The characteristic values may be parameters representing an integral value (area) of each waveform, a length of one waveform, a rise angle of the waveform, an inner angle of the waveform at the position of the peak point P, and a waveform shape calculated by fitting or the like. These characteristic values have correlation with positions on the axis of distance L (turn positions, strokes), and correlation with time taken for one reciprocating training action (i.e., a total time of T1 and T2 which corresponds to the length of a base of the triangular waveform). Therefore, like the peak points P, these characteristic values may also be used as an index indicating variation in turn positions and the like and their increase/decrease tendency. It is also possible to evaluate with use of these characteristic values, relationship between each waveform corresponding to one unit of a training action (variation and tendency) and to determine adequacy of the load thereby.

(Types of Training Exercise)

Note that in the embodiment, leg press was selected as a training action performed with the training apparatus 10. However, the present invention is not limited to this selection. For example, the present invention is also applicable to training apparatuses for performing various types of training actions, such as hip abduction, rowing, and leg extension. The present invention is also applicable to training apparatuses used to perform various training activities to strengthen muscle force of the upper half of the body and to perform training for regularly moving the arm, the shoulder, the elbow, the wrist, the fingers, and other various parts of the upper half and lower half of the body in rehabilitation involving exercise for the limbs.

More specifically, in the foregoing embodiment, in response to a position of the movable unit 16, waveforms plotted on a two-dimensional plane made up of the position (distance from a start point) and time are analyzed based on a plurality of the peak points P and based on one waveform. In the case of a simple reciprocating motion such as leg press, the analysis can be performed simply by determining one axis in the distance direction.

However, the present invention is not necessarily limited to a simple one-dimensional reciprocating motion like leg press (exercise only in the X-axis direction). In the case of performing two-dimensional or three-dimensional exercise, it is possible to select rectangular coordinate axes such as X-axis, Y-axis, and Z-axis as an independent coordinate system, and to perform analysis based on a plurality of the peak points P and analysis based on one waveform on each axis as in the case of the embodiment. It is to be noted that the training action may include not only linear reciprocating motions but also rounded reciprocating motions, such as repeating rotation at a definite angle in a reciprocating manner. Even in such a case, a waveform shown in FIG. 2 and other drawings can be extracted by setting displacement (operating distance) as a vertical axis and time as a horizontal axis.

Various training activities other than leg press may be implemented with a hardware configuration of FIG. 1 including the arithmetic unit 20, the training apparatus 10, the exercise state detector 22, the storage device 26, and the exercise load changing device 28, as with, the configuration explained in the foregoing embodiment.

(Method for Detecting Exercise State)

It is to be noted that detection of the exercise state may be implemented by detecting displacement of a portion (displacement unit) of the muscle training machine 12 which is displaced during training, or by detecting displacement of a training target region of the trainee (user 2) (such as an angle and a stretched length of the leg in the embodiment) in response to a training action.

The configuration of a sensor for detecting a training action of the user is not limited to the encoder 22a. Various sensing technologies may be used to detect a position, displacement, a velocity, an acceleration, an angular velocity, an angular acceleration, and other physical values as electric, mechanical, and other various physical information. In detection of the exercise state, the acceleration of a training action may be detected with use of an acceleration sensor. For example, the acceleration sensor can be used for smoothness determination, symmetry determination, or the like. More specifically, the acceleration may be measured by attaching an acceleration sensor to body regions (the arm, the shoulder, the elbow, the wrist, the fingers, and other various parts of the upper half and lower half of the body) which are displaced in response to a training action.

Moreover, a displacement locus by a training action (more specifically a two-dimensional locus or a plane locus, and a three-dimensional locus or a locus of three-dimensional space) may be detected by a sensing technology with use of, for example, various sensors such as a motion sensor. By comparing these detected data with specified reference data (reference values and reference patterns), magnitude of deviation (difference) between an actual training action and a specified action (an expected action at a present stage or a standard or ideal action) may be calculated, and the calculation result may be used for load control.

(Program Recording Medium, Program, and Training Method)

Note that in the present invention, the control process, the arithmetic process, the determination process, and other processes explained in this embodiment may be provided in the form of being stored in CD-ROMs, DVD-ROMs, and other program recording media. It may also be possible to distribute the program as a single product. The control, the analyzing method, and the contents of the processes performed in the above-described embodiment may be implemented as an invention of "the training method".

REFERENCE SIGNS LIST 2 user
10 training apparatus
12 muscle training machine
16 movable unit
20 arithmetic unit
22 exercise state detector
22a encoder
22b encoder signal detector
26 storage device
28 exercise load changing device
29 weights
30 input unit
32 display unit

The invention claimed is:

1. A training apparatus, comprising:
a training machine configured to have a displacement unit displaced according to a training action and a load generation unit that imparts a load to a trainee during the training action;
detection means configured to detect displacement of the displacement unit; and
arithmetic means configured to:
(i) acquire, for a plurality of waveforms, at least one characteristic value selected from a peak point possessed by a waveform corresponding to one unit of a training action which waveform is included in the displacement detected by the detection means on a time axis, an integral value of the waveform, a length of the waveform, a rise angle of the waveform, an angle at a peak point position of the waveform, and a parameter representing a predetermined waveform shape,
(ii) evaluate, based on a relationship between the acquired characteristic values, at least one of a variation of the acquired characteristic values, a transition tendency of the acquired characteristic values, and a deviation of an average value of the acquired characteristic values from a predetermined value, and
(iii) execute, based on the evaluation, at least one of control of the load generation unit, calculation of a load value set in the load generation unit, and notification of a result of the evaluation.

2. The training apparatus according to claim 1, wherein the arithmetic means includes:
peak point specification means configured to specify, as the characteristic value for each of the plurality of waveforms, a peak point that is a point where a displacement coordinate component reaches a maximum value; and
calculation means configured to control the load generation unit or to calculate the load value which is to be set in the load generation unit based on at least one of a magnitude of variation of the specified peak points, an increase/decrease tendency of the specified peak points, and a difference between an average value of the specified peak points and a predetermined displacement, according to a positional relationship between the specified peak points found in displacement coordinates.

3. The training apparatus according to claim 1, wherein the training action is an action including a reciprocating motion,
the training apparatus further comprises unit waveform evaluation means configured to calculate, based on at least one property selected from time, a velocity, a smoothness, and a symmetry of a waveform corresponding to one unit of a reciprocating motion in the training action which waveform is included in the displacement detected by the detection means, a load value which is to be set in the load generation unit, and
the arithmetic means includes means configured to control the load generation unit or to calculate the load value which is set in the load generation unit by using the load value calculated by the unit waveform evaluation means.

4. The training apparatus according to claim 3, wherein the unit waveform evaluation means includes:
symmetry determination means configured to determine whether or not symmetry of the one waveform is lower than a predetermined degree and to determine the symmetry based on a temporal relationship between a movement in one direction and a return movement of the training action; and
pattern determination means configured to determine, if a waveform low in symmetry is determined in the symmetry determination means, whether or not the waveform low in symmetry matches a predetermined pattern or approximates to the predetermined pattern at or above a predetermined level, and
the training apparatus further comprises: output means configured to output a predetermined signal if the waveform low in symmetry matches or approximates to the predetermined pattern at or above the predetermined level.

5. A training apparatus, comprising:
a training machine configured to have a displacement unit displaced according to a training action and a load generation unit that imparts a load to a trainee during the training action;
a detector configured to detect displacement of the displacement unit; and
an arithmetic unit configured to:
(i) acquire, for a plurality of waveforms, at least one characteristic value selected from a peak point possessed by a waveform corresponding to one unit of a training action which waveform is included in the displacement detected by the detection means on a time axis, an integral value of the waveform, a length of the waveform, a rise angle of the waveform, an angle at a peak point position of the waveform, and a parameter representing a predetermined waveform shape,
(ii) evaluate, based on a relationship between the acquired characteristic values, at least one of a variation of the acquired characteristic values, a transition tendency of the acquired characteristic values, and a deviation of an average value of the acquired characteristic values from a predetermined value, and
(iii) execute, based on the evaluation, at least one of control of the load generation unit, calculation of a load value set in the load generation unit, and notification of a result of the evaluation.

6. The training apparatus according to claim 5, wherein the arithmetic unit is programmed to execute:
a peak point specification process configured to specify, as the characteristic value for each of the plurality of waveforms, a peak point that is a point where a displacement coordinate component reaches a maximum value; and
a calculation process to control the load generation unit or to calculate the load value which is to be set in the load generation unit based on at least one of a magnitude of variation of the specified peak points, an increase/decrease tendency of the specified peak points, and a difference between an average value of the specified peak points and a predetermined displacement, according to a positional relationship between the specified peak points found in displacement coordinates.

7. The training apparatus according to claim 5, wherein the training action is an action including a reciprocating motion, and
the arithmetic unit is programmed to execute: a unit waveform evaluation process to calculate, based on at least one property selected from time, a velocity, a smoothness, and a symmetry of a waveform corresponding to one unit of a reciprocating motion in the training action which waveform is included in the displacement detected by the detection means, a load value which is to be set in the load generation unit, wherein the arithmetic unit controls the load generation unit or calculates the load value which is set in the load generation unit by using the load value by the unit waveform evaluation unit.

8. The training apparatus according to claim 7, wherein the unit waveform evaluation process includes:
a symmetry determination process to determine whether or not symmetry of the one waveform is lower than a predetermined degree and to determine the symmetry based on a temporal relationship between a movement in one direction and a return movement of the training action; and
a pattern determination process to determine, if a waveform low in symmetry is determined in the symmetry determination process, whether or not the waveform low in symmetry matches a predetermined pattern or approximates to the predetermined pattern at or above a predetermined level, and
the training apparatus outputs a predetermined signal if the waveform low in symmetry matches or approximates to the predetermined pattern at or above the predetermined level.

* * * * *